US006562635B1

(12) United States Patent
Lensing et al.

(10) Patent No.: US 6,562,635 B1
(45) Date of Patent: May 13, 2003

(54) METHOD OF CONTROLLING METAL ETCH PROCESSES, AND SYSTEM FOR ACCOMPLISHING SAME

(75) Inventors: Kevin R. Lensing, Austin, TX (US); James Broc Stirton, Austin, TX (US); Matthew A. Purdy, Austin, TX (US)

(73) Assignee: Advanced Micro Devices, Inc., Austin, TX (US)

( * ) Notice: Subject to any disclaimer, the term of this patent is extended or adjusted under 35 U.S.C. 154(b) by 0 days.

(21) Appl. No.: 10/083,710

(22) Filed: Feb. 26, 2002

(51) Int. Cl.[7] ............................................... H01L 21/00
(52) U.S. Cl. ............................................................. 438/7
(58) Field of Search ................................. 438/8, 5, 6, 7, 438/16

(56) References Cited

U.S. PATENT DOCUMENTS 5,867,276 A * 2/1999 McNeil et al. ............... 356/445
6,100,985 A * 8/2000 Scheiner et al. ............. 356/381
6,291,254 B1 * 9/2001 Chou et al. .................... 438/18

* cited by examiner

*Primary Examiner*—David Nelms
*Assistant Examiner*—Quoc Hoang
(74) *Attorney, Agent, or Firm*—Williams, Morgan & Amerson, P.C.

(57) ABSTRACT

A method of using scatterometry measurements to determine and control conductive interconnect profiles is disclosed. In one embodiment, the method comprises providing a library of optical characteristic traces, each of which correspond to a grating structure comprised of a plurality of conductive interconnects having a known profile, providing a substrate having at least one grating structure formed thereabove, the formed grating structure comprised of a plurality of conductive interconnects having an unknown profile, and illuminating the formed grating structure. The method further comprises measuring light reflected off of the grating structure to generate an optical characteristic trace for the formed grating structure and determining a profile of the gate electrode structures comprising the formed grating structure by correlating the generated optical characteristic trace to an optical characteristic trace from the library. In another embodiment, the method disclosed herein comprises comparing a generated optical characteristic trace of conductive interconnects having an unknown profile to a target trace established for conductive interconnects having an ideal or acceptable profile.

57 Claims, 4 Drawing Sheets

(Prior Art) Figure 1B

METHOD OF CONTROLLING METAL ETCH PROCESSES, AND SYSTEM FOR ACCOMPLISHING SAME

CROSS-REFERENCE TO RELATED APPLICATION

This application is related to application Ser. No. 09/865,821 filed May 25, 2001 now U.S. Pat. No. 6,433,871.

BACKGROUND OF THE INVENTION

1. Field of the Invention

This invention relates generally to semiconductor fabrication technology, and, more particularly, to a method of controlling metal etch processes, and a system for accomplishing same.

2. Description of the Related Art

There is a constant drive within the semiconductor industry to increase the operating speed of integrated circuit devices, e.g., microprocessors, memory devices, and the like. This drive is fueled by consumer demands for computers and electronic devices that operate at increasingly greater speeds. This demand for increased speed has resulted in a continual reduction in the size of semiconductor devices, e.g., transistors. That is, many components of a typical field effect transistor (FET), e.g., channel length, junction depths, gate insulation thickness, and the like, are reduced. For example, all other things being equal, the smaller the channel length of the transistor, the faster the transistor will operate. Thus, there is a constant drive to reduce the size, or scale, of the components of a typical transistor to increase the overall speed of the transistor, as well as integrated circuit devices incorporating such transistors.

Typically, integrated circuit devices are comprised of hundreds or millions of transistors formed above a semiconducting substrate. By way of background, an illustrative field effect transistor 10, as shown in FIG. 1, may be formed above a surface 15 of a semiconducting substrate or wafer 11 comprised of doped-silicon. The substrate 11 may be doped with either N-type or P-type dopant materials. The transistor 10 may have a doped polycrystalline silicon (polysilicon) gate electrode 14 formed above a gate insulation layer 16. The gate electrode 14 and the gate insulation layer 16 may be separated from doped source/drain regions 22 of the transistor 10 by a dielectric sidewall spacer 20. The source/drain regions 22 for the transistor 10 may be formed by performing one or more ion implantation processes to introduce dopant atoms, e.g., arsenic or phosphorous for NMOS devices, boron for PMOS devices, into the substrate 11. Shallow trench isolation regions 18 may be provided to isolate the transistor 10 electrically from neighboring semiconductor devices, such as other transistors (not shown). Additionally, although not depicted in FIG. 1, a typical integrated circuit device is comprised of a plurality of conductive interconnects, such as conductive lines and conductive contacts or vias, positioned in multiple layers of insulating material formed above the substrate 11.

The structure and composition of such conductive interconnects has become very important in modern integrated circuit devices. For example, given the drive for integrated circuit devices with greater operating speeds, circuit designers take great care in designing such conductive interconnects to insure that electrical signals may propagate as quickly as possible within an integrated circuit device. In particular, it is important that the electrical resistance of the conductive interconnects is as low as possible. As a result, conductive interconnects are typically comprised of a metal, such as aluminum, titanium, copper, etc., due to the relatively low resistance of these materials. More particularly, copper has become increasingly popular as an interconnect material due to its very attractive electrical characteristics.

In addition to the material selected for the conductive interconnects, it is important that the physical size of the interconnect structure not be inadvertently reduced during fabrication because such reductions may lead to an undesirable increase in the resistance of the conductive interconnects. Unfortunately, such reductions do occur in semiconductor fabrication, and they can be very difficult to detect, as will be discussed in connection with FIGS. 1B–1C. FIG. 1B is a cross-sectional side view of an illustrative conductive interconnect, i.e., a conductive line 17, formed in a layer of insulating material 19, e.g., silicon dioxide. Also depicted in FIG. 1B are two bottom barrier metal layers 21 and 23, a top barrier layer 25, and a cap layer 27. As will be recognized by those skilled in the art, the structure depicted in FIG. 1B is illustrative only of a portion of a single level of multiple levels of conductive interconnects within a typical integrated circuit device. FIG. 1C is a top view of the structure depicted in FIG. 1B.

As can be seen in FIG. 1B, the conductive line 17 exhibits severe undercutting, as indicated by arrows 31, relatively to an ideal, rectangular shape for the conductive line 17, as indicated by dashed lines 33. Such undercutting is primarily due to the problems associated with etching metals, such as aluminum. Typically, a chlorine-based plasma etch process may be performed to etch aluminum conductive interconnects. However, when etching metals, such as aluminum, such an etching process tends to be somewhat isotropic in nature, thereby producing the undercutting 31 of the conductive interconnect 17. Efforts are made to introduce a passivant during the etching process used to form the conductive interconnect to reduce the undercutting of the conductive interconnect, but such efforts do not completely reduce the undercutting of the conductive interconnect.

Additionally, such undercutting, and the extent of such undercutting, may be difficult to detect with existing metrology tools and methods. In etching the cap layer 27 and the other barrier metal layers, it is relatively easy to achieve a very anisotropic profile of those layers due to the materials used for such layers. These various etching processes result in the structure depicted in FIG. 1B. Unfortunately, commonly employed metrology tools and techniques may not be able to adequately detect the existence or extent of undercutting of the conductive interconnect 17 in such structures. For example, a scanning electron microscope (SEM) may be employed after the conductive interconnect 17 is formed to obtain information about the physical size, i.e., the width, of the conductive interconnect 17. The SEM may be used to take a "top-down" look at the conductive interconnect 17, as indicated by the arrows 35. However, due to the close proximity of the conductive interconnects 17 within a given layer, the existence of the cap layer 27 and the upper barrier layer 25, and the inherent nature of the SEM, the data obtained by the SEM does not reveal the true or entire profile of the conductive interconnect 17. Thus, the profile of the conductive interconnect 17 cannot readily be examined using an SEM.

Typically, one or more production or test wafers that are representative of one or more lots of wafers are eventually cross-sectioned and analyzed to detect the existence of undercutting problems with the conductive interconnects. However, it takes days or weeks to generate results from such destructive testing techniques. During this time, additional conductive interconnects may be being manufactured on additional wafers with undesirable undercutting characteristics, thereby tending to increase the resistance of such conductive interconnects. Moreover, the results of such destructive testing techniques are not provided in sufficient time to provide meaningful and relatively rapid feedback to allow more precise control of the processing parameters used to form the conductive interconnects 17.

The present invention is directed to a method and system that may solve, or at least reduce, some or all of the aforementioned problems.

SUMMARY OF THE INVENTION

The present invention is generally directed to a method of controlling metal etch processes, and a system for accomplishing same. In one illustrative embodiment, the method comprises providing a library of optical characteristic traces, each of which correspond to a grating structure comprised of a plurality of conductive interconnects having a known profile, providing a substrate having at least one grating structure formed thereabove, the formed grating structure comprised of a plurality of conductive interconnects having an unknown profile, and illuminating the grating structure formed above the substrate. The method further comprises measuring light reflected off of the grating structure to generate an optical characteristic trace for the formed grating structure and determining a profile of the conductive interconnects comprising the formed grating structure by correlating the generated optical characteristic trace to an optical characteristic trace from the library. In a further embodiment, the method comprises modifying at least one parameter of at least one etching process used to form conductive interconnects on a subsequently processed substrate based upon the determined profile of the conductive interconnects comprising the formed grating structure.

In another aspect, the present invention is directed to a method whereby a generated trace of a grating structure comprised of a plurality of conductive interconnects having an unknown profile is compared to a target trace established for a grating structure comprised of conductive interconnects having an acceptable profile. In one illustrative embodiment, the method comprises providing a library comprised of at least one optical characteristic trace, one of which is a target trace that corresponds to a grating structure comprised of a plurality of conductive interconnects having a known target profile, and providing a substrate having at least one grating structure formed thereabove, the formed grating structure comprised of a plurality of conductive interconnects having an unknown profile. The method further comprises illuminating the grating structure formed above the substrate, measuring light reflected off of the grating structure to generate an optical characteristic trace for the formed grating structure, and comparing the generated optical characteristic trace to the target trace. In a further embodiment, the method further comprises determining, based upon the comparison of the generated optical characteristic trace and the target trace, at least one parameter of at least one etching process used to form conductive interconnects on a subsequently processed substrate.

BRIEF DESCRIPTION OF THE DRAWINGS

The invention may be understood by reference to the following description taken in conjunction with the accompanying drawings, in which like reference numerals identify like elements, and in which:

FIGS. 1B–1C are, respectively, a cross-sectional view and a top view of an illustrative conductive interconnect;

Figure 1A:
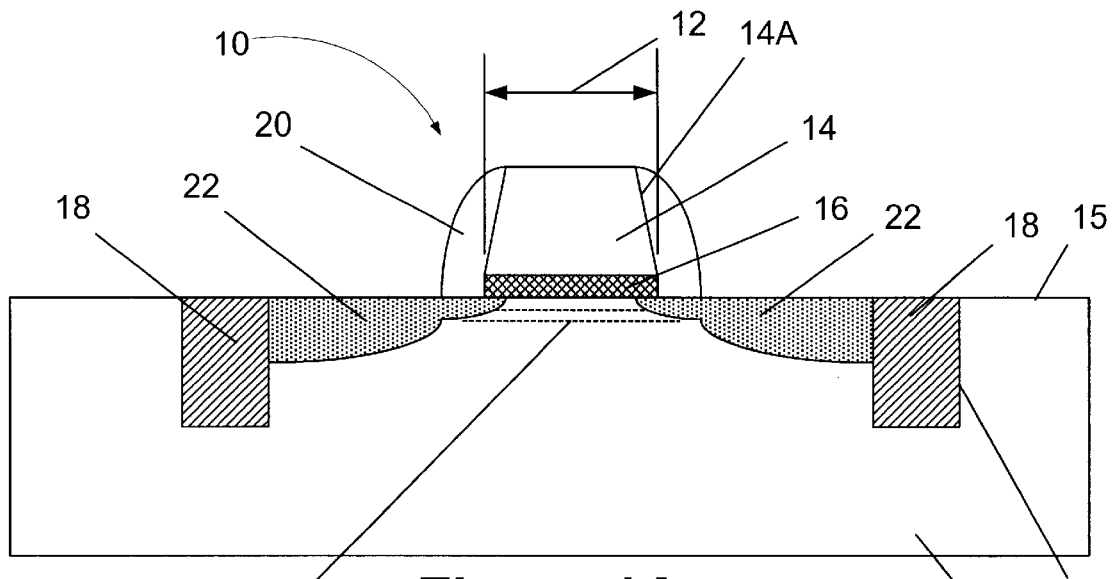
FIG. 1A is a cross-sectional view of an illustrative prior art transistor.
Figure 1C:
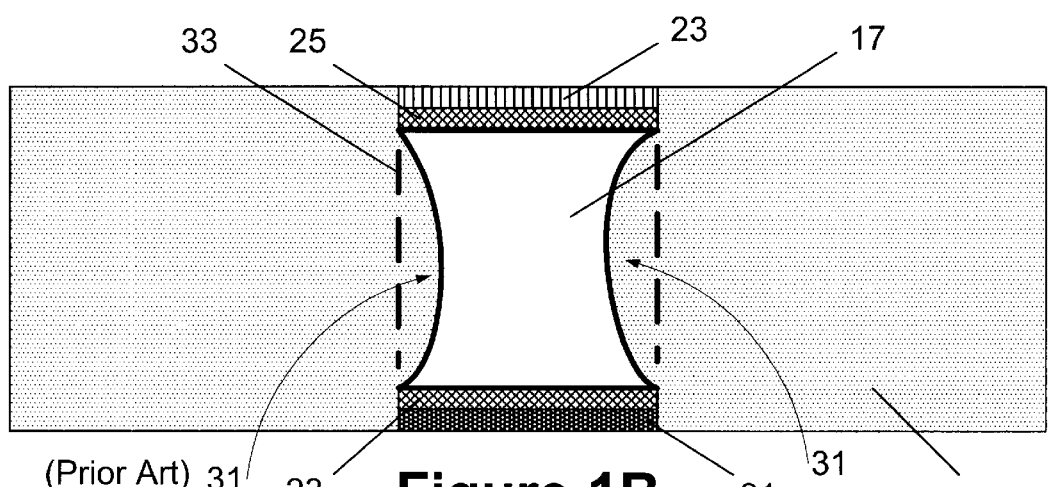
Figure 1C:
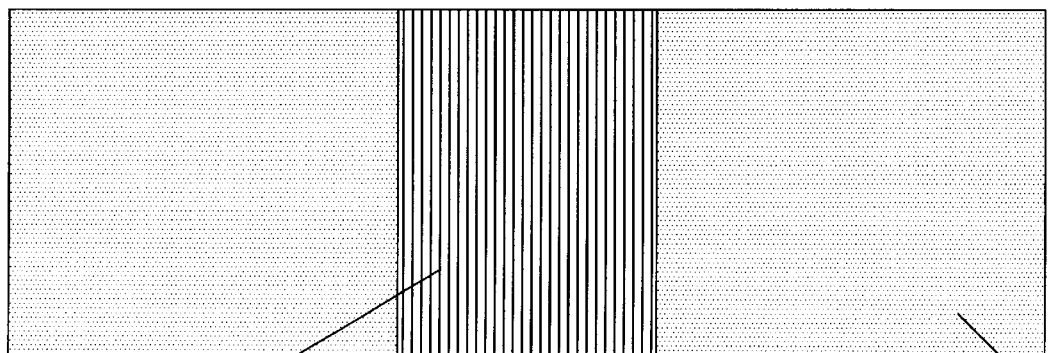

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF THE INVENTION

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

The present invention will now be described with reference to the attached figures. Although the various regions and structures of a semiconductor device are depicted in the drawings as having very precise, sharp configurations and profiles, those skilled in the art recognize that, in reality, these regions and structures are not as precise as indicated in the drawings. Additionally, the relative sizes of the various features and doped regions depicted in the drawings may be exaggerated or reduced as compared to the size of those features or regions on fabricated devices. Nevertheless, the attached drawings are included to describe and explain illustrative examples of the present invention.

In general, the present invention is directed to a method of controlling metal etch processes, and a system for accomplishing same. As will be readily apparent to those skilled in the art upon a complete reading of the present application, the present method is applicable to a variety of technologies, e.g., NMOS, PMOS, CMOS, etc., and it is readily applicable to a variety of devices, including, but not limited to, logic devices, memory devices, etc.

In general, in one embodiment, the present invention involves the formation of a grating structure comprised of a plurality of conductive interconnects 30, taking scatterometric measurements of those conductive interconnects 30 to determine the profile of the conductive interconnects 30, and determining one or more parameters of an etching process to be used to form additional conductive interconnects 30 on one or more subsequently processed substrates.

Figure 2A:
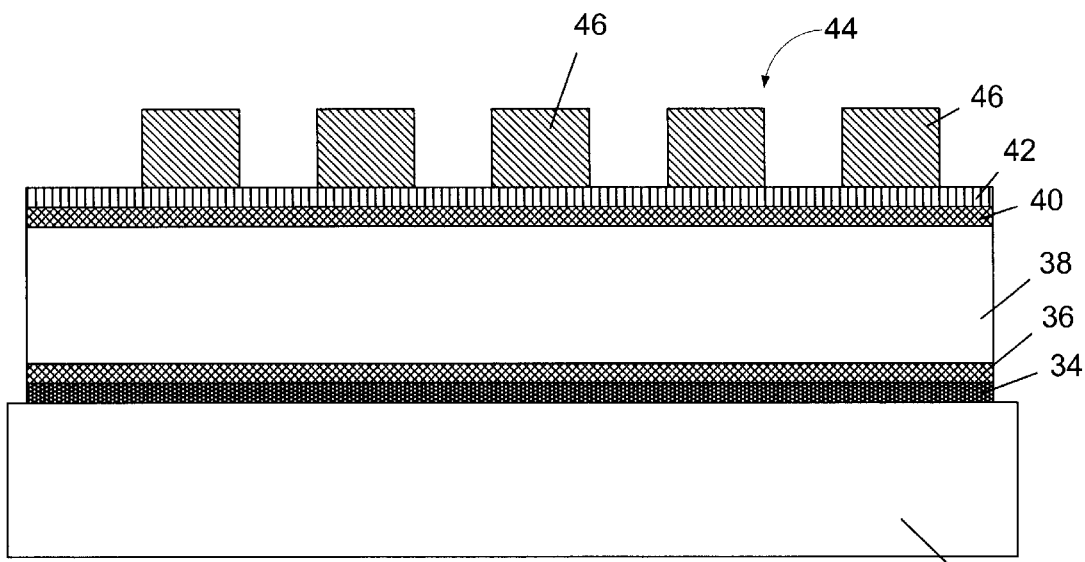
FIGS. 2A–2C are views depicting an illustrative process flow for forming conductive interconnects.
Figure 2B:
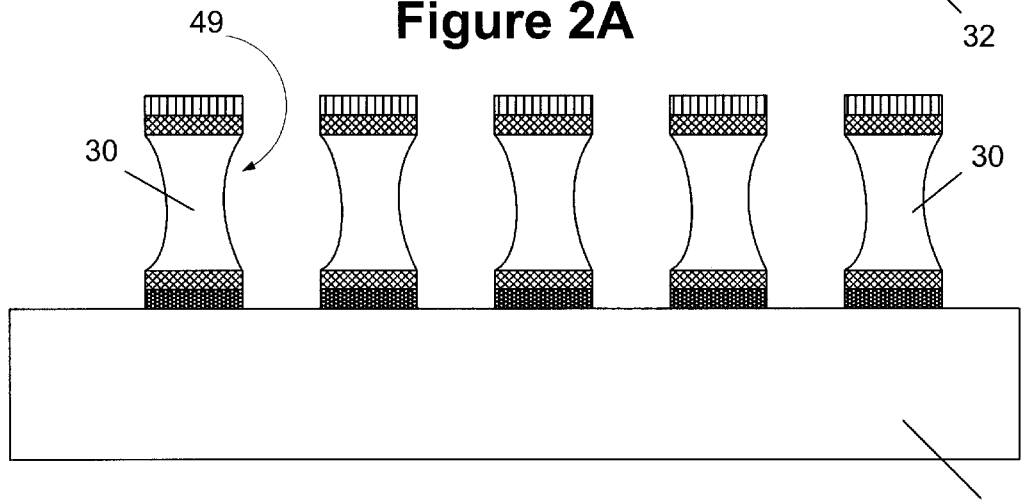
Figure 2C:
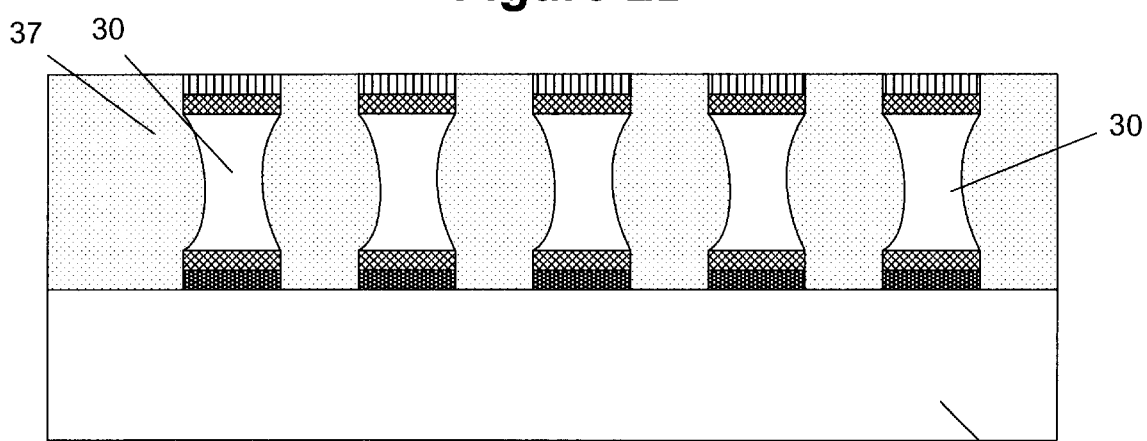

FIGS. 2A–2C depict one illustrative embodiment of a process flow that may be employed in forming conductive interconnects 30 useful in an integrated circuit device. As shown in FIG. 2A, the structure 32 may be representative of a previously formed layer of material or of a semiconducting substrate. In the case where the structure 32 is a layer of insulating material, it may have a plurality of conductive interconnects formed therein, although those structures are not depicted in FIG. 2A. To form the conductive interconnects 30, the process involves the formation of a first layer 34 comprised of, for example, titanium, a second layer 36 comprised of, for example, titanium nitride, a third layer 38 comprised of a conductive interconnect material such as aluminum, a fourth layer 40 comprised of, for example, titanium nitride, and a fifth hard mask layer 42 comprised of, for example, silicon dioxide. Also depicted in FIG. 2A is a patterned layer of photoresist 44 comprised of a plurality of photoresist features 46. The various layers depicted in FIG. 2A may be formed using a variety of known processing techniques and equipment, and they may be comprised of a variety of different materials. Thus, the particular materials and methods depicted and described herein should not be considered a limitation of the present invention unless such limitations are clearly set forth in the appended claims.

Next, as shown in FIG. 2B, using the patterned layer of photoresist 44 as a mask, one or more etching processes are performed to form the conductive interconnects 30. In FIG. 2B, the patterned layer of photoresist 44 has been removed by performing an ashing process. In the depicted embodiment, the conductive interconnect 30 exhibits undercutting, as indicated by arrows 49. Next, as shown in FIG. 2C, a layer of insulating material 37, e.g., silicon dioxide, is added to fill in the spaces between the conductive interconnects 30 and one or more planarization processes may be performed to arrive at the structure depicted in FIG. 2C. Additional layers of conductive interconnects may be formed above the structure depicted in FIG. 2C.

Figure 3A:
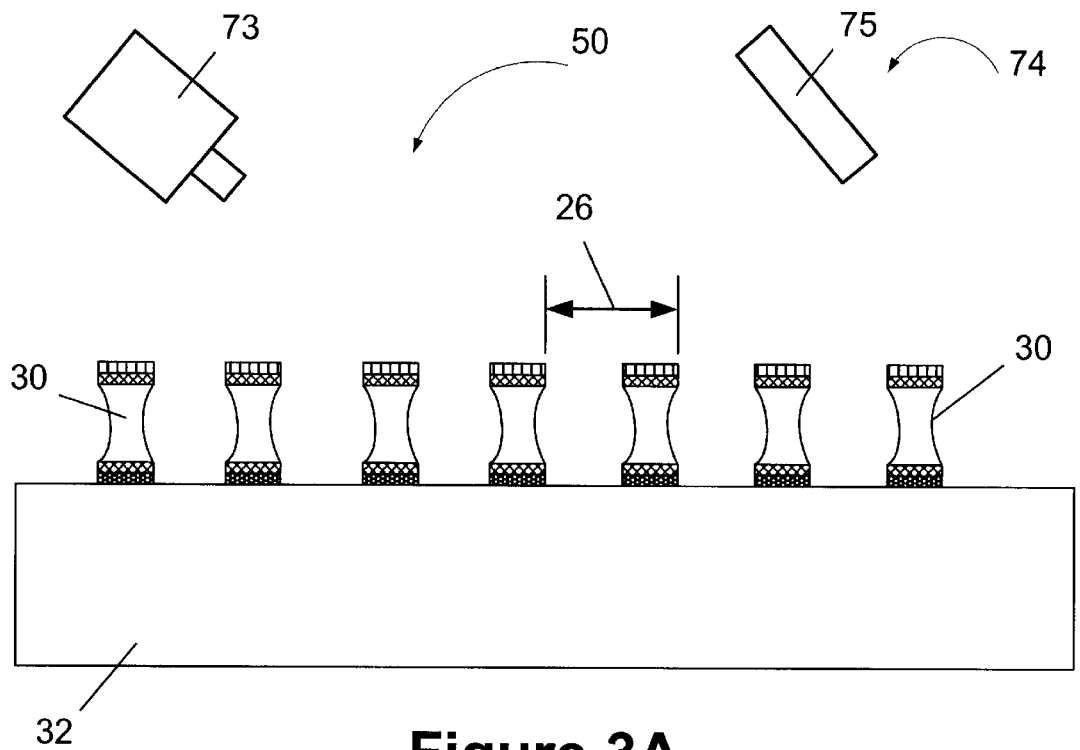
FIGS. 3A–3B depict an illustrative grating structure comprised of a plurality of conductive interconnects, and scatterometry tool illuminating such structures in accordance with one aspect of the present invention.
Figure 3B:
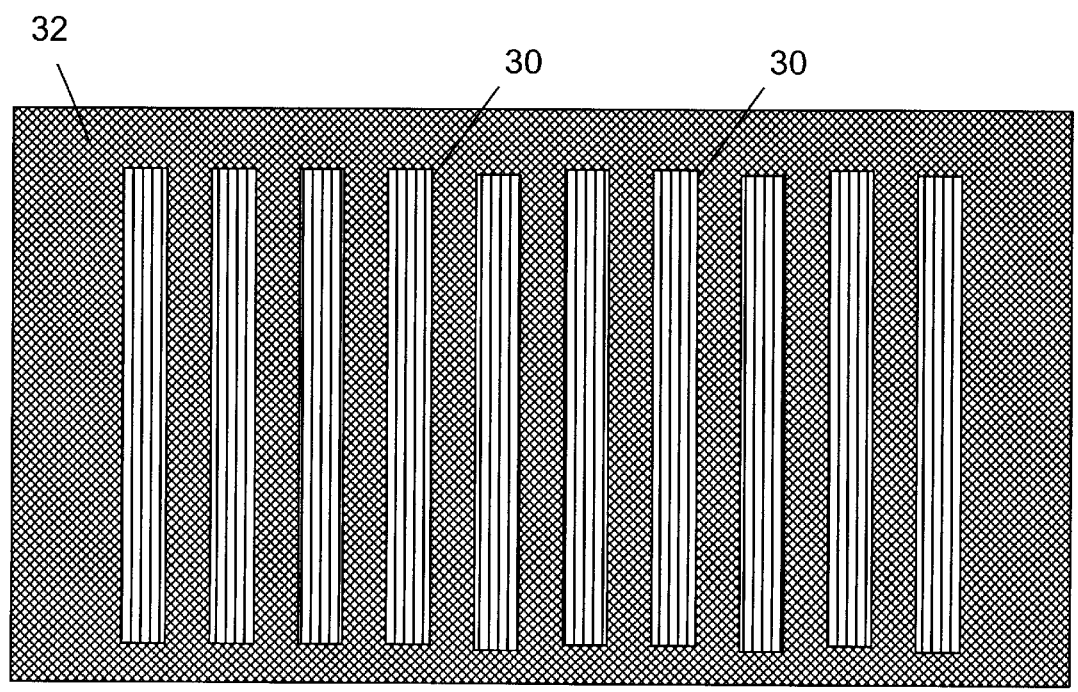

In one embodiment, as shown in FIGS. 3A–3B, the present invention involves the formation of a plurality of conductive interconnects 30 to define a grating structure 50. The conductive interconnects 30 will be manufactured using the same design rules and dimensions as the conductive interconnects on production devices at the interconnect level of interest. The grating structure 50 may be formed in the scribe line of a wafer, and the grating structure 50 will be formed at the same time the conductive interconnects 30 are being formed for production devices formed on the wafer. A plurality of such grating structures 50 may be formed at various locations across a surface of the wafer. The size, shape and configuration of the grating structure 50 may be varied as a matter of design choice. For example, the grating structure 50 may be formed in an area having approximate dimensions of 100 $\mu$m×120 $\mu$m, and it may be comprised of approximately 500–1500 conductive interconnects 30 (depending upon the selected pitch).

Also depicted in FIG. 3A is an illustrative scatterometry tool 74 comprised of a representative light source 73 and a detector 75. Ultimately, the grating structure 50 will be measured using scatterometric techniques, and these measurements will be used to determine and/or confirm the profile of the conductive interconnects 30 comprising the grating structure 50. Moreover, the scatterometry measurements may be used to determine, confirm and/or control one or more parameters of an etching process used to form conductive interconnects 30 on one or more subsequently processed wafers.

Figure 4:
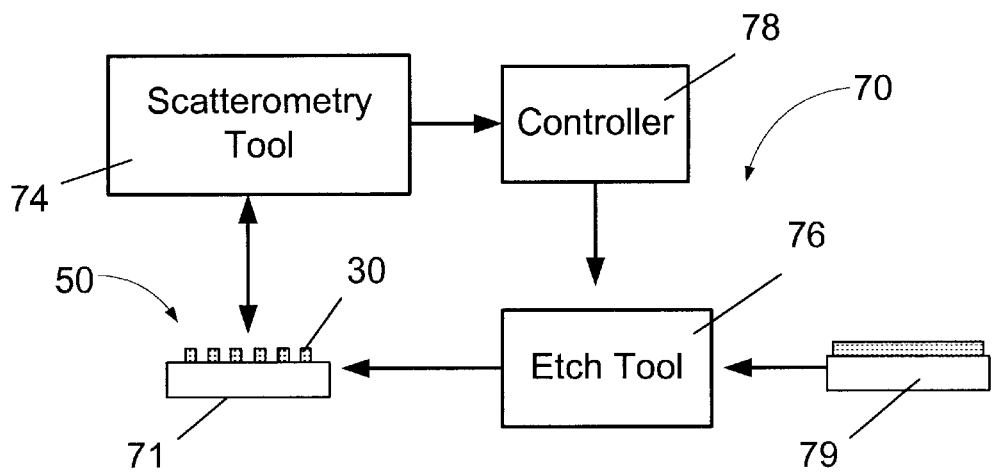
FIG. 4 depicts an illustrative embodiment of a system in accordance with one embodiment of the present invention.

An illustrative system 70 that may be used in one embodiment of the present invention is shown in FIG. 4. The system 70 is comprised of a scatterometry tool 74, an etch tool 76, and a controller 78. As indicated in FIG. 4, the wafer 71 is representative of one or more wafers that has previously been processed in the etch tool 76. The wafers 71 have a grating structure 50 comprised of a plurality of conductive interconnects 30 formed thereabove. The wafer 79 represents wafers that are yet to be processed in the etch tool 76.

A variety of scatterometry tools 74 may be used with the present invention, e.g., so-called 2$\theta$-type systems and lens-type scatterometry tools. The scatterometry tool 74 may use white light, or some other wavelength or combination of wavelengths, depending on the specific implementation. Typically, the scatterometry tool 74 will generate an incident beam that has a wide spectral composition and wherein the intensity of the light changes slowly in comparison to changes in wavelength. The angle of incidence of the light may also vary, depending on the specific implementation. The profile traces generated by the scatterometry tool 74 may be based upon a comparison of light intensity to wavelength (for white light, fixed angle type scatterometry tools) or a comparison of intensity to incident angle (for angle resolved systems that use a single light source).

Figure 2D:
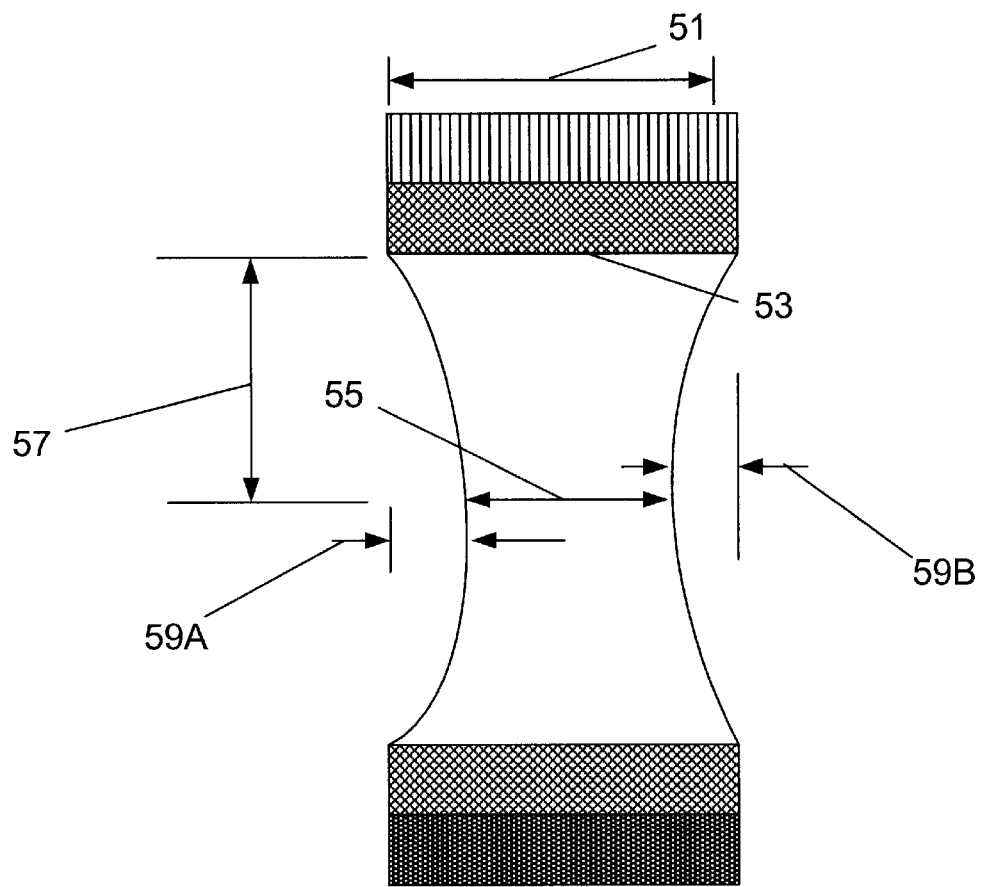
FIG. 2D is an enlarged, exaggerated cross-sectional view of an illustrative conductive interconnect.

Through use of scatterometry, a characteristic signature or profile trace, associated with a particular profile of the conductive interconnects 30, may be calculated (using Maxwell's equations) for a vast variety, if not all, possible combinations of profiles readily anticipated by the design process. These profile traces may be stored in a library. The scatterometry profile trace may be based on a variety of characteristics of the conductive interconnects 30. For example, with reference to FIG. 2D, the optical characteristic trace may be based upon the width 51 of the conductive interconnects 30 at the top surface 53 as compared to the width 55 of the conductive interconnects 30 at a depth 37 that equates to approximately 50% of the thickness of the conductive interconnects 30. Other characteristics such as the total amount of undercutting, as indicated by the sum of the dimensions 59A, 59B, or the area of the conductive interconnects 30 may also be used as the basis for the optical characteristic traces for the conductive interconnect 30 profiles.

Variations in one or more of the characteristics of the conductive interconnect 30 profile will cause a significant change in the diffraction characteristics of the incident light from the light source 73 of the scatterometry tool 74. Thus, using Maxwell's equations, a unique profile trace may be established for each unique conductive interconnect 30 profile anticipated by the design process. A library of profile traces corresponding to each anticipated gate electrode profile may be calculated and stored in a library. Through this technique, each trace in the library represents a grating structure 50 comprised of conductive interconnects 30 having a known profile. If desired, the profiles of the conductive interconnects 30 for each of the traces in the library of gate electrode profile traces may be confirmed using a variety of destructive metrology tests. For example, the actual profile of the conductive interconnects 30 represented by a trace in the library may be confirmed by cross-sectioning the conductive interconnects 30 and observing and measuring characteristics of the profile of the conductive interconnects 30 using a scanning electron microscope. Obviously, the number of conductive interconnect 30 profiles used to create the library may vary as a matter of design choice. Moreover, the larger the number of profiles, the larger will be the library containing the profiles.

The present invention may be employed to correlate or match a measured or generated profile trace of a grating structure 50 comprised of a plurality of conductive interconnects 30 having an unknown profile to a library of such profiles, each of which corresponds to a grating structure 50 comprised of conductive interconnects 30 having a particular known profile. That is, in one embodiment, the scatterometry tool 74 is used to measure and generate a profile trace for a given grating structure 50 comprised of a plurality of conductive interconnects 30 of an unknown profile. The scatterometry tool 74 may measure one or more grating structures 50 on a given wafer in a lot or even generate a profile trace for each grating structure 50 in the lot, depending on the specific implementation. Moreover, the profile traces from a sample of the grating structures 50 may be averaged or otherwise statistically analyzed. The scatterometry tool 74 (or some other controller resident within the manufacturing plant, e.g., controller 78) compares the measured profile trace (i.e., individual or averaged) to a library of profile traces with known conductive interconnect profiles to correlate or approximately match the current measured profile trace with a trace in the library. When a match is confirmed, the scatterometry tool 74 (or other controller) may then provide data as to the profile of the conductive interconnect 30 in the measured grating structure 50. For example, the scatterometry tool 74 may output data, based upon the matched profile trace in the library, indicating that the conductive interconnects 30 in the measured grating structure 50 have a width at the mid-thickness depth of a certain value. Alternatively, the data output may express a ratio between the width at the mid-thickness depth as compared to the width 28 at the top surface 27 of the gate electrode structures 14. A variety of data output criteria and format are possible.

Based upon these comparisons, the previously unknown profile of the conductive interconnects 30 comprising the measured grating structure 50 may be determined. Additionally, based upon the determined profile of the conductive interconnects 30, the controller 78, if needed, may adjust one or more parameters of an etching process to be performed to form conductive interconnects on subsequently processed wafers 79 in the etch tool 76. For example, one or more parameters, such as gas composition, gas flow rates, pressure, temperature, etc., may be varied.

In another embodiment, the measured or generated trace of the grating structure 50 may be compared to a target trace selected from the library for a grating structure 50 comprised of conductive interconnects 30 having a known and desired, or acceptable, target profile. For example, a target trace may be calculated for a grating structure 50 comprised of conductive interconnects 30 having an ideal or acceptable profile using Maxwell's equations, and that target trace may be stored in the library. Thereafter, a measured trace of a grating structure 50 comprised of conductive interconnects. 30 having an unknown profile are compared to the target trace. Based upon this comparison, a relatively rough approximation of the quality of the process performed may be determined. That is, by comparing the measured trace to the target trace, it may be determined if the process is producing conductive interconnects 30 having a profile sufficiently close to the ideal or acceptable profile such that further matching of the measured trace with an additional trace from the library is unwarranted. Using this technique, an initial determination may be made as to the acceptability of the profile of the conductive interconnects 30 as compared to a target profile. Of course, this step may be performed in addition to the matching or correlating of a measured trace to a trace from the library as described above. Thus, one particularly illustrative embodiment of the present invention involves performing a rough pass/fail test comparing the sample profile to a "golden" or target profile. Only failing profiles move on to full profile matching, possibly followed by manipulation of one or more parameters of the etch process used to form conductive interconnects 30 on one or more subsequently processed wafers. For example, using a means squared error analytical to compare the measured spectra to the target trace, if the difference between the two spectra exceed a preselected value or range of values, then the measured trace fails, and additional matching may be performed.

The optical measurements of the grating structure 50 may be performed on any desired number of grating structures 50 and wafers. For example, such measurements may be performed on all wafers in one or more lots, or on a representative number of wafers in a given lot, and these results may then be used to determine or vary one or more parameters, e.g., process gases, flow rates, pressure, temperature, etc., of the etching process performed in the etch tool 76 to form conductive interconnects 30 on one or more subsequently processed wafers. A single substrate may combine a plurality of grating structures 50, and they may be spaced out above the surface of the substrate.

Control equations may be employed to adjust the operating recipe of the etch tool 76 in situations where the methods described herein indicate that an adjustment is warranted. The control equations may be developed empirically using commonly known linear or non-linear techniques. The controller 78 may automatically control the operating recipes of the etch tool 76 used to perform one or more etching processes on the subsequently processed wafers 79. Through use of the present invention, the extent and magnitude of variations in gate electrode profiles may be reduced.

In the illustrated embodiments, the controller 78 is a computer programmed with software to implement the functions described herein. Moreover, the functions described for the controller 78 may be performed by one or more controllers spread through the system. For example, the controller 78 may be a fab level controller that is used to control processing operations throughout all or a portion of a semiconductor manufacturing facility. Alternatively, the controller 78 may be a lower level computer that controls only portions or cells of the manufacturing facility. Moreover, the controller 78 may be a stand-alone device, or it may reside on the etch tool 76. However, as will be appreciated by those of ordinary skill in the art, a hardware controller (not shown) designed to implement the particular functions may also be used.

Portions of the invention and corresponding detailed description are presented in terms of software, or algorithms and symbolic representations of operations on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be understood, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" or "displaying" or the like, refer to the actions and processes of a computer system, or similar electronic computing device, that manipulates and transforms data represented as physical, electronic quantities within the computer system's registers and memories into other data similarly represented as physical quantities within the computer system memories or registers or other such information storage, transmission or display devices.

An exemplary software system capable of being adapted to perform the functions of the controller 78, as described, is the Catalyst system offered by KLA Tencor, Inc. The Catalyst system uses Semiconductor Equipment and Materials International (SEMI) Computer Integrated Manufacturing (CIM) Framework compliant system technologies, and is based on the Advanced Process Control (APC) Framework. CIM (SEMI E81-0699—Provisional Specification for CIM Framework Domain Architecture) and APC (SEMI E93-0999—Provisional Specification for CIM Framework Advanced Process Control Component) specifications are publicly available from SEMI.

The present invention is generally directed to a method of using scatterometry measurements to determine and control conductive interconnect profiles. In one illustrative embodiment, the method comprises providing a library of optical characteristic traces, each of which correspond to a grating structure 50 comprised of a plurality of conductive interconnects 30 having a known profile, providing a substrate having at least one grating structure 50 formed thereabove, the formed grating structure 50 being comprised of a plurality of conductive interconnects 30 having an unknown profile, and illuminating the grating structure 50 formed above the substrate. The method further comprises measuring light reflected off of the grating structure 50 to generate an optical characteristic trace for the formed grating structure 50 and determining a profile of the conductive interconnects 30 comprising the formed grating structure 50 by correlating or matching the generated optical characteristic trace to an optical characteristic trace from the library. In a further embodiment, the method comprises modifying at least one parameter of at least one etching process used to form conductive interconnects 30 on a subsequently processed substrate based upon the determined profile of the conductive interconnects 30 comprising the formed grating structure 50.

In another aspect, the present invention is directed to a method of comparing a generated optical characteristic trace to a target trace. In one illustrative embodiment, the method comprises providing a library comprised of at least one optical characteristic trace, one of which is a target trace that corresponds to a grating structure comprised of a plurality of conductive interconnects having a known target profile, and providing a substrate having at least one grating structure formed thereabove, the formed grating structure comprised of a plurality of conductive interconnects having an unknown profile. The method further comprises illuminating the grating structure formed above the substrate, measuring light reflected off of the grating structure to generate an optical characteristic trace for the formed grating structure, and comparing the generated optical characteristic trace to the target trace. In a further embodiment, the method comprises determining, based upon the comparison of the generated optical characteristic trace and the target trace, at least one parameter of at least one etching process used to form conductive interconnects on a subsequently processed substrate. In yet a further embodiment, the method comprises modifying, based upon the comparison of the generated optical characteristic trace and the target trace, at least one parameter of at least one etching process used to form conductive interconnects on a subsequently processed substrate.

The present invention is also directed to a system for accomplishing the illustrative methods described herein. In one embodiment, the system 70 is comprised of a scatterometry tool 74, an etch tool 76 and a controller 78. The scatterometry tool 74 is adapted to make scatterometric measurements of a grating structure 50 comprised of a plurality of conductive interconnects 30 having an unknown profile and generate an optical characteristic trace for the grating structure 50. The scatterometry tool 74 may be further used to compare the generated optical characteristic trace to a target optical characteristic trace (from the library) or to correlate or match the generated optical characteristic trace to an optical trace in the library. The controller 78 may then be used to control one or more parameters of one or more etching processes used in forming conductive interconnects 30 on subsequently processed wafers.

Through use of the present invention, better process control may be achieved in modern integrated circuit manufacturing facilities. Additionally, the present invention may enable more precise formation of conductive interconnects of transistors employed in integrated circuit devices, thereby improving device performance and increasing production yields.

The particular embodiments disclosed above are illustrative only, as the invention may be modified and practiced in different but equivalent manners apparent to those skilled in the art having the benefit of the teachings herein. For example, the process steps set forth above may be performed in a different,order. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

What is claimed is:

1. A method, comprising:

providing a library of optical characteristic traces, each of which correspond to a grating structure comprised of a plurality of conductive interconnects having a known profile;

providing a substrate having at least one grating structure formed thereabove, said formed grating structure comprised of a plurality of conductive interconnects having an unknown profile;

illuminating said grating structure formed above said substrate;

measuring light reflected off of said grating structure to generate an optical characteristic trace for said formed grating structure; and determining a profile of said conductive interconnects comprising said formed grating structure by correlating said generated optical characteristic trace to an optical characteristic trace from said library.

2. The method of claim 1, further comprising modifying at least one parameter of at least one etching process used to form conductive interconnects on a subsequently processed substrate based upon the determined profile of said conductive interconnects comprising said formed grating structure.

3. The method of claim 1, wherein providing a library of optical characteristic traces comprises providing a library of optical characteristic traces, each of said plurality of said traces corresponding to a grating structure comprised of conductive interconnects having a profile that exhibits undercutting.

4. The method of claim 1, wherein providing a substrate having at least one grating structure formed thereabove comprises providing a substrate having at least one grating structure formed in a scribe line of said substrate.

5. The method of claim 1, wherein providing a substrate having at least one grating structure formed thereabove comprises providing a substrate having a plurality of grating structures formed thereabove.

6. The method of claim 2, wherein modifying at least one parameter of at least one etching process used to form conductive interconnects on a subsequently processed substrate comprises modifying at least one of a gas composition, a gas flow rate, a temperature, a pressure and a duration of said at least one etching process.

7. The method of claim 1, wherein providing a library of optical characteristic traces comprises providing a library of optical characteristic traces, each of which correspond to a grating structure comprised of a plurality of conductive interconnects having a profile that corresponds to an anticipated profile for said conductive interconnects.

8. The method of claim 1, wherein said grating structure formed above said provided substrate is formed in an area having dimensions of approximately 100×120 $\mu$m.

9. A method, comprising:

providing a library of optical characteristic traces, each of which correspond to a grating structure comprised of a plurality of conductive interconnects having a known profile;

providing a substrate having at least one grating structure formed thereabove, said formed grating structure comprised of a plurality of conductive interconnects having an unknown profile;

illuminating said grating structure formed above said substrate;

measuring light reflected off of said grating structure to generate an optical characteristic trace for said formed grating structure;

determining a profile of said conductive interconnects comprising said formed grating structure by correlating said generated optical characteristic trace to an optical characteristic trace from said library; and modifying at least one parameter of at least one etching process used to form conductive interconnects on a subsequently processed substrate based upon the determined profile of said conductive interconnects comprising said formed grating structure.

10. The method of claim 9, wherein providing a library of optical characteristic traces comprises providing a library of optical characteristic traces, each of said plurality of said traces corresponding to a grating structure comprised of conductive interconnects having a profile that exhibits undercutting.

11. The method of claim 9, wherein providing a substrate having at least one grating structure formed thereabove comprises providing a substrate having at least one grating structure formed in a scribe line of said substrate.

12. The method of claim 9, wherein providing a substrate having at least one grating structure formed thereabove comprises providing a substrate having a plurality of grating structures formed thereabove.

13. The method of claim 10, wherein modifying at least one parameter of at least one etching process used to form conductive interconnects on a subsequently processed substrate comprises modifying at least one of a gas composition, a gas flow rate, a temperature, a pressure and a duration of said at least one etching process.

14. The method of claim 9, wherein providing a library of optical characteristic traces comprises providing a library of optical characteristic traces, each of which correspond to a grating structure comprised of a plurality of conductive interconnects having a profile that corresponds to an anticipated profile for said conductive interconnects.

15. The method of claim 9, wherein said grating structure formed above said provided substrate is formed in an area having dimensions of approximately 100×120 $\mu$m.

16. A method, comprising:

providing a library of optical characteristic traces, each of which correspond to a grating structure comprised of a plurality of conductive interconnects having a known profile, each of said plurality of said traces corresponding to a grating structure comprised of conductive interconnects having a profile that exhibits undercutting;

providing a substrate having at least one grating structure formed thereabove, said formed grating structure comprised of a plurality of conductive interconnects having an unknown profile;

illuminating said grating structure formed above said substrate;

measuring light reflected off of said grating structure to generate an optical characteristic trace for said formed grating structure;

determining a profile of said conductive interconnects comprising said formed grating structure by correlating said generated optical characteristic trace to an optical characteristic trace from said library; and modifying at least one parameter of at least one etching process used to form conductive interconnects on a subsequently processed substrate based upon the determined profile of said conductive interconnects comprising said formed grating structure.

17. The method of claim 16, wherein providing a substrate having at least one grating structure formed thereabove comprises providing a substrate having at least one grating structure formed in a scribe line of said substrate.

18. The method of claim 16, wherein providing a substrate having at least one grating structure formed thereabove comprises providing a substrate having a plurality of grating structures formed thereabove.

19. The method of claim 16, wherein modifying at least one parameter of at least one etching process used to form conductive interconnects on a subsequently processed substrate comprises modifying at least one of a gas composition, a gas flow rate, a temperature, a pressure and a duration of said at least one etching process.

20. The method of claim 16, wherein providing a library of optical characteristic traces comprises providing a library of optical characteristic traces, each of which correspond to a grating structure comprised of a plurality of conductive interconnects having a profile that corresponds to an anticipated profile for said conductive interconnects.

21. The method of claim 16, wherein said grating structure formed above said provided substrate is formed in an area having dimensions of approximately 100×120 $\mu$m.

22. A method, comprising:
providing a library comprised of at least one optical characteristic trace, one of which is a target trace that corresponds to a grating structure comprised of a plurality of conductive interconnects having a known target profile;
providing a substrate having at least one grating structure formed thereabove, said formed grating structure comprised of a plurality of conductive interconnects having an unknown profile;
illuminating said grating structure formed above said substrate;
measuring light reflected off of said grating structure to generate an optical characteristic trace for said formed grating structure; and
comparing said generated optical characteristic trace to said target trace.

23. The method of claim 22, further comprising determining, based upon said comparison of said generated optical characteristic trace and said target trace, at least one parameter of at least one etching process used to form conductive interconnects on a subsequently processed substrate.

24. The method of claim 22, further comprising modifying, based upon said comparison of said generated optical characteristic trace and said target trace, at least one parameter of at least one etching process used to form conductive interconnects on a subsequently processed substrate.

25. The method of claim 22, wherein said target trace corresponds to a grating structure comprised of a plurality of conductive interconnects exhibiting substantially no undercutting.

26. The method of claim 22, wherein providing a library comprised of at least one optical characteristic trace comprises providing a library comprised of a plurality of optical characteristic traces, each of said plurality of said traces corresponding to a grating structure comprised of conductive interconnects having a profile that exhibits undercutting, and each of a second plurality of said traces corresponding to a grating structure comprised of gate electrode structures having a profile that exhibits footing.

27. The method of claim 22, wherein providing a substrate having at least one grating structure formed thereabove comprises providing a substrate having at least one grating structure formed in a scribe line of said substrate.

28. The method of claim 22, wherein providing a substrate having at least one grating structure formed thereabove comprises providing a substrate having a plurality of grating structures formed thereabove.

29. The method of claim 24, wherein modifying at least one parameter of at least one etching process used to form conductive interconnects on a subsequently processed substrate comprises modifying at least one of a gas composition, a gas flow rate, a temperature, a pressure and a duration of said at least one etching process.

30. The method of claim 22, wherein providing a library comprised of at least one optical characteristic trace comprises providing a library comprised of a plurality of optical characteristic traces, each of which correspond to a grating structure comprised of a plurality of conductive interconnects having a profile that corresponds to an anticipated profile for said conductive interconnects.

31. The method of claim 22, wherein said grating structure formed above said provided substrate is formed in an area having dimensions of approximately 100×120 $\mu$m.

32. The method of claim 22, wherein said library comprises a plurality of optical characteristic traces, each of which correspond to a grating structure comprised of a plurality of conductive interconnects having a known profile.

33. The method of claim 22, further comprising comparing the generated trace and the target trace and performing additional matching of said generated trace to at least one additional optical characteristic trace from said library if the difference between said generated trace and said target trace exceeds a preselected value.

34. The method of claim 32, further comprising:
determining a profile of said conductive interconnects comprising said formed grating structure by correlating said generated optical characteristic trace to an optical characteristic trace from said library; and
modifying at least one parameter of at least one etching process used to form conductive interconnects on a subsequently processed substrate based upon the determined profile of said conductive interconnects comprising said formed grating structure.

35. A method, comprising:
providing a library comprised of at least one optical characteristic trace, one of which is a target trace that corresponds to a grating structure comprised of a plurality of conductive interconnects having a known target profile;
providing a substrate having at least one grating structure formed thereabove, said formed grating structure comprised of a plurality of conductive interconnects having an unknown profile;
illuminating said grating structure formed above said substrate;
measuring light reflected off of said grating structure to generate an optical characteristic trace for said formed grating structure;
comparing said generated optical characteristic trace to said target trace; and
determining, based upon said comparison of said generated optical characteristic trace and said target trace, at least one parameter of at least one etching process used to form conductive interconnects on a subsequently processed substrate.

36. The method of claim 35, further comprising modifying, based upon said comparison of said generated optical characteristic trace and said target trace, at least one parameter of at least one etching process used to form conductive interconnects on a subsequently processed substrate.

37. The method of claim 35, wherein said target trace corresponds to a grating structure comprised of a plurality of conductive interconnects exhibiting substantially no undercutting.

38. The method of claim 35, wherein providing a library comprised of at least one optical characteristic trace comprises providing a library comprised of a plurality of optical characteristic traces, each of said plurality of said traces corresponding to a grating structure comprised of conductive interconnects having a profile that exhibits undercutting.

39. The method of claim 35, wherein providing a substrate having at least one grating structure formed thereabove comprises providing a substrate having at least one grating structure formed in a scribe line of said substrate.

40. The method of claim 35, wherein providing a substrate having at least one grating structure formed thereabove comprises providing a substrate having a plurality of grating structures formed thereabove.

41. The method of claim 36, wherein modifying at least one parameter of at least one etching process used to form conductive interconnects on a subsequently processed substrate comprises modifying at least one of a gas composition, a gas flow rate, a temperature, a pressure and a duration of said at least one etching process.

42. The method of claim 36, wherein providing a library comprised of at least one optical characteristic trace comprises providing a library comprised of a plurality of optical characteristic traces, each of which correspond to a grating structure comprised of a plurality of conductive interconnects having a profile that corresponds to an anticipated profile for said conductive interconnects.

43. The method of claim 36, wherein said grating structure formed above said provided substrate is formed in an area having dimensions of approximately 100×120 μm.

44. The method of claim 36, wherein said library comprises a plurality of optical characteristic traces, each of which correspond to a grating structure comprised of a plurality of conductive interconnects having a known profile.

45. The method of claim 36, further comprising comparing the generated trace and the target trace and performing additional matching of said generated trace to at least one additional optical characteristic trace from said library if the difference between said generated trace and said target trace exceeds a preselected value.

46. The method of claim 44, further comprising:
determining a profile of said conductive interconnects comprising said formed grating structure by correlating said generated optical characteristic trace to an optical characteristic trace from said library; and
modifying at least one parameter of at least one etching process used to form conductive interconnects on a subsequently processed substrate based upon the determined profile of said conductive interconnects comprising said formed grating structure.

47. A method, comprising:
providing a library comprised of at least one optical characteristic trace, one of which is a target trace that corresponds to a grating structure comprised of a plurality of conductive interconnects having a known target profile;
providing a substrate having at least one grating structure formed thereabove, said formed grating structure comprised of a plurality of conductive interconnects having an unknown profile;
illuminating said grating structure formed above said substrate;
measuring light reflected off of said grating structure to generate an optical characteristic trace for said formed grating structure;
comparing said generated optical characteristic trace to said target trace; and
modifying, based upon said comparison of said generated optical characteristic trace and said target trace, at least one parameter of at least one etching process used to form conductive interconnects on a subsequently processed substrate.

48. The method of claim 47, further comprising determining, based upon said comparison of said generated optical characteristic trace and said target trace, at least one parameter of at least one etching process used to form conductive interconnects on a subsequently processed substrate.

49. The method of claim 47, wherein said target trace corresponds to a grating structure comprised of a plurality of conductive interconnects exhibiting substantially no undercutting.

50. The method of claim 47, wherein providing a substrate having at least one grating structure formed thereabove comprises providing a substrate having at least one grating structure formed in a scribe line of said substrate.

51. The method of claim 47, wherein providing a substrate having at least one grating structure formed thereabove comprises providing a substrate having a plurality of grating structures formed thereabove.

52. The method of claim 47, wherein modifying at least one parameter of at least one etching process used to form conductive interconnects on a subsequently processed substrate comprises modifying at least one of a gas composition, a gas flow rate, a temperature, a pressure and a duration of said at least one etching process.

53. The method of claim 47, wherein providing a library comprised of at least one optical characteristic trace comprises providing a library comprised of a plurality of optical characteristic traces, each of which correspond to a grating structure comprised of a plurality of conductive interconnects having a profile that corresponds to an anticipated profile for said conductive interconnects.

54. The method of claim 47, wherein said grating structure formed above said provided substrate is formed in an area having dimensions of approximately 100×120 μm.

55. The method of claim 47, wherein said library comprises a plurality of optical characteristic traces, each of which correspond to a grating structure comprised of a plurality of conductive interconnects having a known profile.

56. The method of claim 47, further comprising comparing the generated trace and the target trace and performing additional matching of said generated trace to at least one additional optical characteristic trace from said library if the difference between said generated trace and said target trace exceeds a preselected value.

57. The method of claim 55, further comprising:
determining a profile of said conductive interconnects comprising said formed grating structure by correlating said generated optical characteristic trace to an optical characteristic trace from said library; and
modifying at least one parameter of at least one etching process used to form conductive interconnects on a subsequently processed substrate based upon the determined profile of said conductive interconnects comprising said formed grating structure.

* * * * *